United States Patent [19]

Duffett et al.

[11] Patent Number: Plant 5,739

[45] Date of Patent: May 6, 1986

[54] CHRYSANTHEMUM PLANT NAMED SUNBEAM

[75] Inventors: William E. Duffett, Salinas, Calif.; Grace H. Mack, New Canaan, Conn.

[73] Assignee: Yoder Brothers, Inc., Barberton, Ohio

[21] Appl. No.: 653,606

[22] Filed: Sep. 24, 1984

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar named Sunbeam particularly characterized as to uniqueness by the combined characteristics of button capitulum form, formal decorative capitulum type, yellow ray floret color, diameter across face of capitulum up to 2.5 cm., short plant height, semi-spreading branching pattern, average natural season flowering date of September 15, average flowering response period of seven weeks in photoperiodic controlled short day programs, and uniform response with durable color and form in Spring for small pot flowering programs.

3 Drawing Figures

The present invention comprises a new and distinct cultivar of *Chrysanthemum morifolium*, Ramat., named Sunbeam.

Sunbeam is a product of a planned breeding program which had the objective of creating cultivars with decorative capitulum type, button form, short height, spreading branching pattern, durable inflorescence, seven week flowering response period, and yellow ray floret color under outdoor natural season conditions.

Sunbeam was originated from a cross made by Grace H. Mack in a controlled breeding program in New Canaan, Conn. in 1979. The female parent, identified as 76390001, was an unnamed yellow decorative seedling derived from a cross between West Point, disclosed by U.S. Plant Pat. No. 4,517, and an unnamed seedling. The male parent, identified as 77437002, was an unnamed yellow decorative seedling bred from unnamed seedlings.

Sunbeam was discovered and selected as a flowering plant within the progeny of the stated cross by William E. Duffett in September 1980 in an outdoor field in Salinas, Calif. The first act of asexual reproduction of Sunbeam was accomplished when vegetative cuttings were taken from the initial selection in June 1981 by William E. Duffett. Horticultural examination of selected units initiated September 1981 has demonstrated that the combination of characteristics herein disclosed for Sunbeam are firmly fixed and are retained through successive generations of asexual reproduction.

Sunbeam has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers and then moved outdoors under the natural temperature and day length prevailing during July through September. Single pinching was practiced, with all branches and buds retained.

The following traits have been repeatedly observed and are determined to be basic characteristics of Sunbeam which in combination distinguish this chrysanthemum as a new and distinct cultivar:

(1) Button capitulum form.

(2) Formal decorative capitulum type.

(3) Yellow ray floret color.

(4) Diameter across face of capitulum up to 2.5 cm.

(5) Short plant height (requiring 2 long day weeks prior to pinch followed by 3 to 7 long days prior to short days, and 0 to 1 application of 2500 ppm B-9 SP in 7 to 14 days after the beginning of short days to attain a flowered plant height of 25 to 35 cm. in 6″ pots).

(6) Semi-spreading branching pattern.

(7) Average natural season flowering date of September 15.

(8) Average flowering response period of seven weeks in photoperiodic controlled flowering programs.

(9) Uniform response with durable color and form in Spring for small pot flowering programs.

The accompanying photographic drawings show typical inflorescence and leaf characteristics of Sunbeam. Sheet 1 is a color photograph of Sunbeam. Sheet 2 is a black and white photograph showing three views of the inflorescence of Sunbeam. Sheet 3 is a black and white photograph showing the upper surface and under surface of the leaves of Sunbeam at three stages of development (mature, intermediate, immature).

Of the many commercial cultivars known to the present inventors, the most similar in comparison to Sunbeam is West Point, disclosed by U.S. Plant Pat. No. 4,517.

Reference is made to attached Chart A which compares certain characteristics of Sunbeam with the same characteristics of West Point. It will be noted that in comparison to West Point, Sunbeam has smaller inflorescence diameter, earlier natural flowering date, superior color retention and deeper color development. The inflorescence type and form, plant height and branching pattern are similar.

In the following description, color references are made to The Royal Horticultural Society Colour Chart. The color values were determined between 10:00 A.M. and 10:15 A.M. on May 2, 1984 under 380 foot-candle light intensity at Salinas, Calif.

Classification:

*Botanical.*—*Chrysanthemum morifolium,* Ramat., cv Sunbeam.

*Commercial.*—Garden variety and button spray pot mum.

I. INFLORESCENCE

A. Capitulum:

*Form.*—Button.

*Type.*—Formal decorative.

*Permanence.*—14 days.

*Diameter across face.*—2.0 to 2.5 cm.

B. Corolla of ray florets:

*Color (general tonality from a distance of three meters).*—Yellow.

*Upper surface.*—6A, 6B.

*Under surface.*—6D.

*Shape.*—Short, wide.

C. Reproductive organs:

*Androecium.*—Present disc florets; scant pollen.

*Gynoecium.*—Present both ray and disc florets.

D. Corolla of disc florets:

*Color (mature).*—1A.

*Color (immature).*—154B.

II. PLANT

A. General appearance:

*Height.*—Short.

*Branching pattern.*—Semi-spreading.

B. Foliage:

*Color (upper surface).*—147A.

*Color (under surface).*—147B.

*Shape.*—Moderately lobed. Moderately serrated.

CHART A

| COMPARISON OF SUNBEAM AND WEST POINT | | |
|---|---|---|
| CULTIVAR | RAY FLORET COLOR | CAPITULUM FORM AND TYPE |
| SUNBEAM | YELLOW | BUTTON FORMAL DECORATIVE |
| WEST POINT | MEDIUM YELLOW | BUTTON FORMAL DECORATIVE |

CHART A-continued

| COMPARISON OF SUNBEAM AND WEST POINT | | |
|---|---|---|
| CULTIVAR | AVERAGE NATURAL SEASON FLOWER DATE | PLANT HEIGHT |
| SUNBEAM | SEPTEMBER 15 | SHORT |
| WEST POINT | SEPTEMBER 28 | SHORT |

| CULTIVAR | BRANCHING PATTERN AND SPREAD | DIAMETER ACROSS FACE OF CAPITULUM |
|---|---|---|
| SUNBEAM | SEMI-SPREADING | 2 to 2.5 cm. |
| WEST POINT | SPREADING | 2.5 to 4 cm. |

| CULTIVAR | PERMANENCE OF FORM AND COLOR |
|---|---|
| SUNBEAM | FORM - 14 DAYS<br>COLOR - 14 to 21 DAYS |
| WEST POINT | FORM - 14 to 21 DAYS<br>COLOR - 7 to 10 DAYS |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., named Sunbeam, as described and illustrated, and particularly characterized as to uniqueness by the combined characteristics of button capitulum form, formal decorative capitulum type, yellow ray floret color, diameter across face of capitulum up to 2.5 cm., short plant height, semi-spreading branching pattern, average natural season flowering date of September 15, average flowering response period of seven weeks in photoperiodic controlled short day programs, and uniform response with durable color and form in Spring for small pot flowering programs.

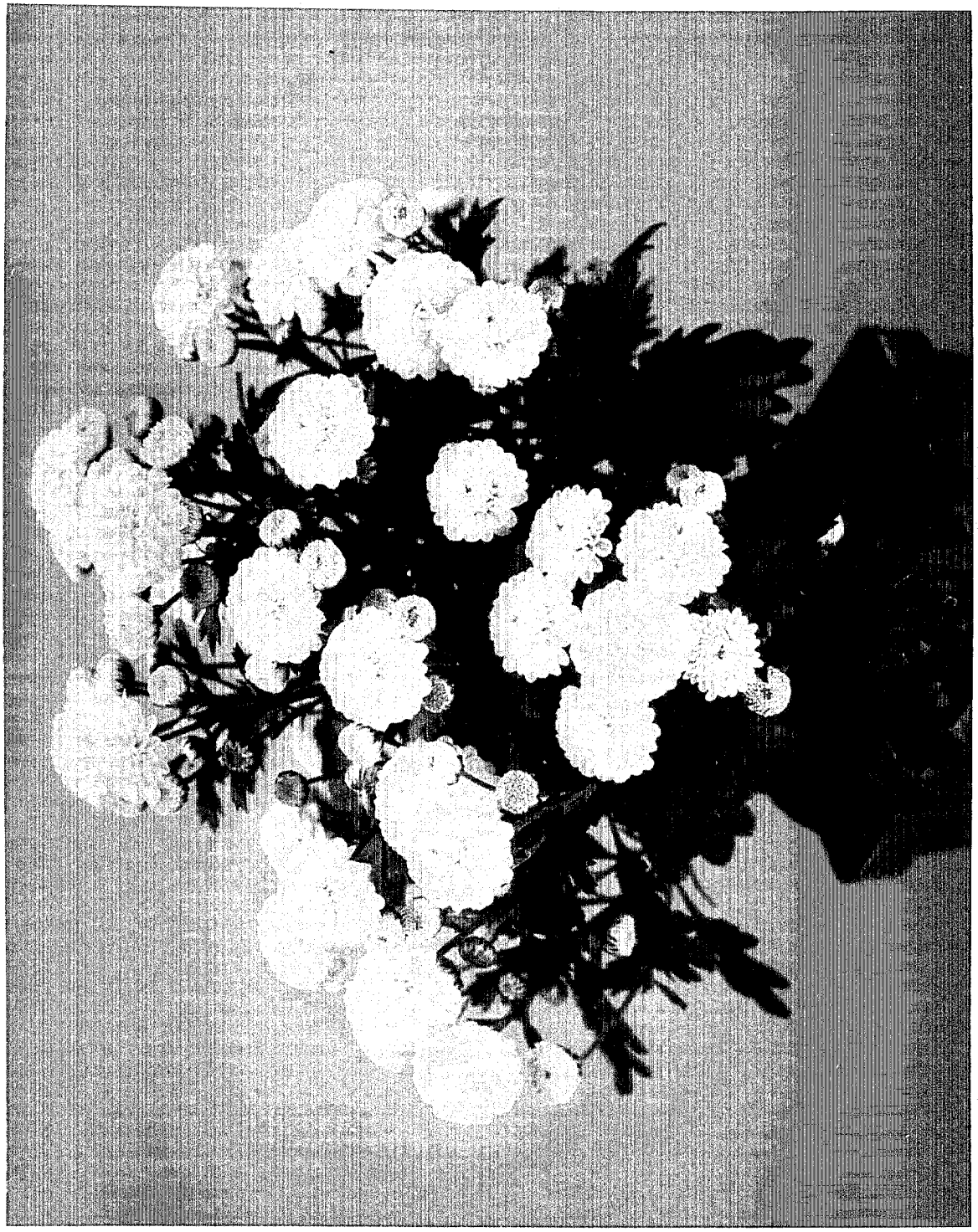

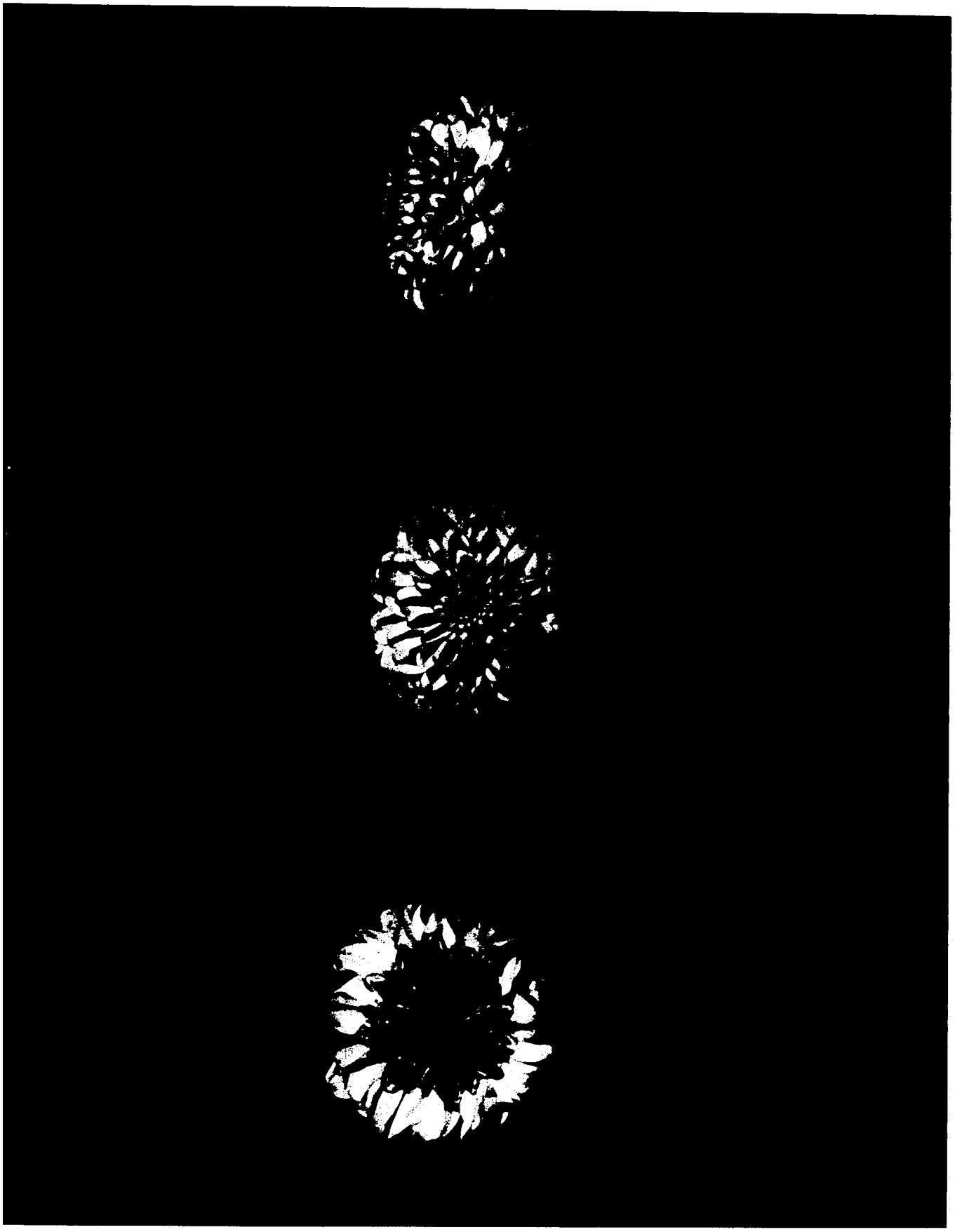

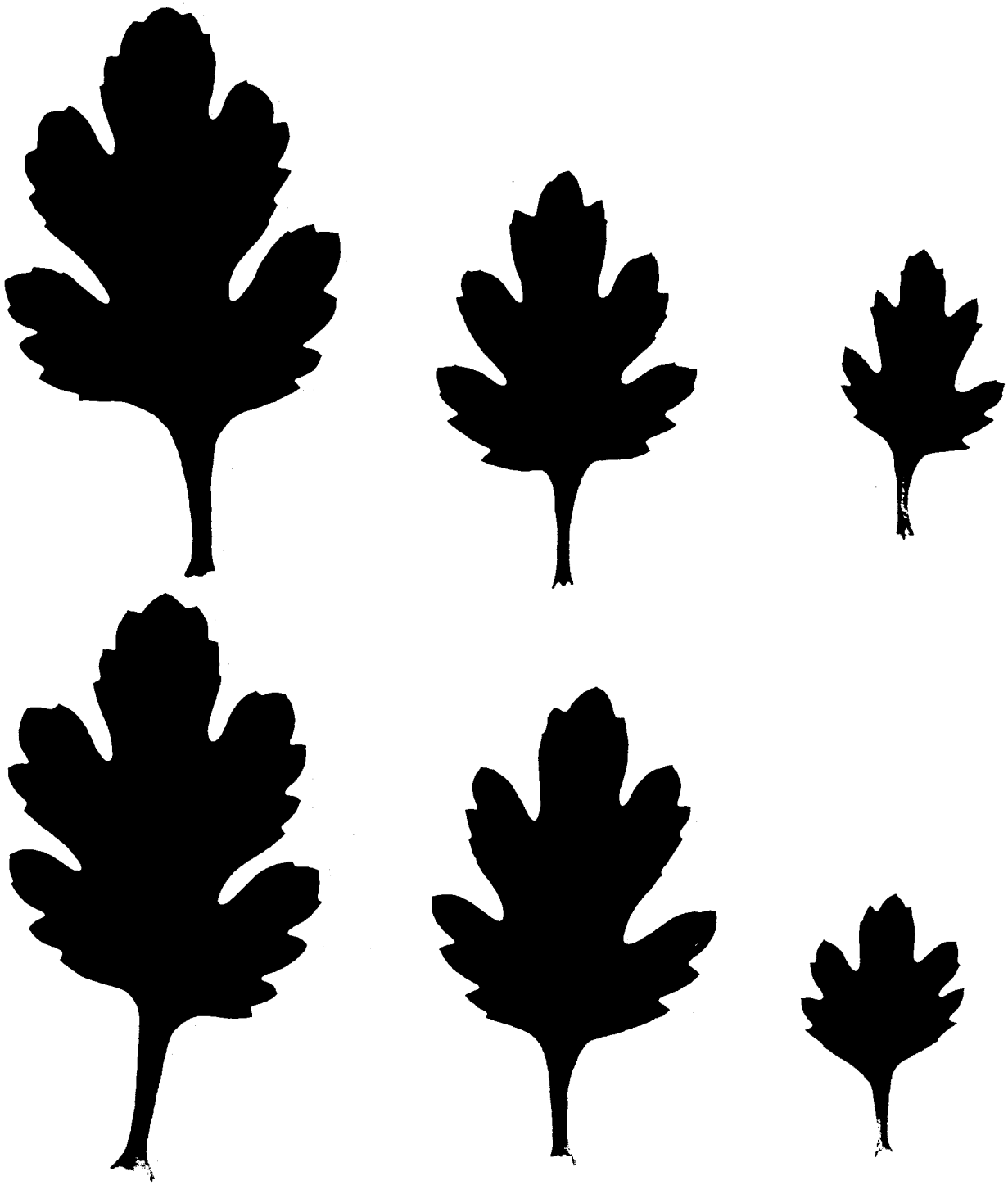

* * * * *